(12) United States Patent
Farone et al.

(10) Patent No.: US 6,384,266 B1
(45) Date of Patent: May 7, 2002

(54) METHOD OF SYNTHESIS OF BETAINE ESTERS

(75) Inventors: William A. Farone, Irvine; Tracy Palmer, Rancho Santa Margarita, both of CA (US)

(73) Assignee: Applied Power Concepts, Inc., Anaheim, CA (US)

( * ) Notice: Subject to any disclaimer, the term of this patent is extended or adjusted under 35 U.S.C. 154(b) by 0 days.

(21) Appl. No.: 09/655,977

(22) Filed: Sep. 5, 2000

(51) Int. Cl.$^7$ ............................................. C07C 229/00
(52) U.S. Cl. ....................................... 560/155; 562/575
(58) Field of Search ........................... 560/155; 562/575

(56) References Cited

U.S. PATENT DOCUMENTS

| | | | | |
|---|---|---|---|---|
| 2,519,573 A | * | 8/1950 | Hoglan | ........................ 260/501 |
| 4,020,100 A | | 4/1977 | Evans et al. | ........... 260/501.13 |
| 4,076,743 A | | 2/1978 | Koch et al. | ............ 260/501.13 |
| 5,961,999 A | * | 10/1999 | Bimczok et al. | ............. 424/401 |

FOREIGN PATENT DOCUMENTS

DE   4229655   *  3/1994   .........  C07C/229/00

OTHER PUBLICATIONS

Toyoki Kunitake et al, "Chiral, Synthetic Bilayer Membranes", Chem. Lett., (1979), pp. 1413–1416.*
K. Brendel et al, "The Resolution of (±)–Carnitine and the Synthesis of Acylcarntines", Biochim. biophys. Acta, vol. 137 (1967), pp. 98–106.*

Merck Index, Ninth Edition (1976), No. 1209 "Betaine Hydrochloride", p. 156.*

The Merck Index (12$^{th}$ Edition), 1225 (1996).

Holden, Can. J. Chem. 62, 574–579 (1984).

Lindstedt et al, Antimicrob. Agents and Chemother. 34(10), 1949–1954, (1990).

Edebo et al, Industrial Applns. Of Surfactants III, 184–207 (1992).

Dery, K–O Encycl. Chem. Tech. (4$^{th}$ Ed.), 20, 739–767 (1996).

Reck, K–O Concise Encycl. Chem. Tech., 984 (1985).

Merianos, Disinfect. Steriliz. And Preservat. (4$^{th}$ ed.), 225–255 (1991).

* cited by examiner

Primary Examiner—Paul J. Killos
(74) Attorney, Agent, or Firm—Cynthia H. O'Donohue

(57) ABSTRACT

The present invention relates to an environmentally acceptable method of producing glycine betaine esters that produces no toxic by-products during the synthesis. The method produces only product, recyclable material for reuse in the process, and recovered material which can be sold for uses, such as fertilizer.

7 Claims, 1 Drawing Sheet

METHOD OF SYNTHESIS OF BETAINE ESTERS

FIELD OF THE INVENTION

The present invention relates to methods of synthesis of betaine esters. More particularly, this invention concerns a method of synthesis of glycine betaine esters which utilizes environmentally acceptable raw materials and a process from which there is little or no waste.

BACKGROUND OF THE INVENTION

Glycine betaine esters are an interesting and useful class of chemical compounds. A typical glycine betaine ester is:

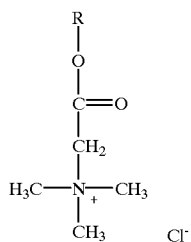

The chain length of the alcohol portion of the ester group, R, can be varied to provide a range of compounds. For the purposes of making betaine esters that will have biocidal and detergent activity the alcohols are derived from the reduction of oil and fat derived fatty acids from about C8 to C22, i.e.

$$CH_3(CH_2)_nCH_2OH$$

where n=6 to 20. The alcohols are esterified with glycine betaine:

The betaine esters are structurally similar to a widely used class of compounds, quaternary ammonium halides, which are used as sanitizing biocides, surface sterilizing agents, fabric softeners and cationic surface-active agents (surfactants). A number of commercially available quaternary ammonium halides are available for these purposes from chemical suppliers such as Rohm America Inc. or Lonza Inc. The synthesis and uses of quaternary ammonium halides are well known, for example see Kirk-Othmer Encyclopedia of Chemical Technology, Fourth Edition. Quaternary ammonium halides, however, are quite toxic and persist in the environment after use.

Researchers at the University of Goteberg in Sweden determined that the glycine betaine esters were a superior substitute for the quaternary ammonium halides. The methods of synthesis for the glycine betaine esters has been quite difficult. Some of these methods are given in U.S. Pat. No. 4,020,100 and U.S. Pat. No. 4,076,743. Expensive and toxic reagents are used to produce these glycine betaine esters. The available synthetic methods relied on the use of a complicated and costly preparation. Most of the methods start with chloroacetic acid and add the cetyl alcohol group as an ester to the chloroacetic acid. The final step in these earlier betaine esters processes is replacing the chlorine with an adduct from trimethylamine.

It is proposed to produce glycine betaine esters conveniently, economically with a process from which there is little or no waste. Additionally the raw materials used during the synthesis would be environmentally acceptable and pose little risk.

SUMMARY OF THE INVENTION

In one aspect the present invention relates to a new environmentally friendly method of synthesis of betaine esters performing the esterification directly.

In another aspect of this instant invention all by-product streams can be either recycled or rendered harmless.

BRIEF DESCRIPTION OF THE DRAWING

The preferred embodiment of this invention, illustrating all its features, will now be discussed in detail. This embodiment depicts the novel and non-obvious process of this invention making, for example, a betaine ester as shown in the accompanying drawing, which is for illustrative purposes only. This drawing includes the following figure (FIG. 1), with like numerals indicating like parts.

DETAILED DESCRIPTION OF THE INVENTION

Figure 1:
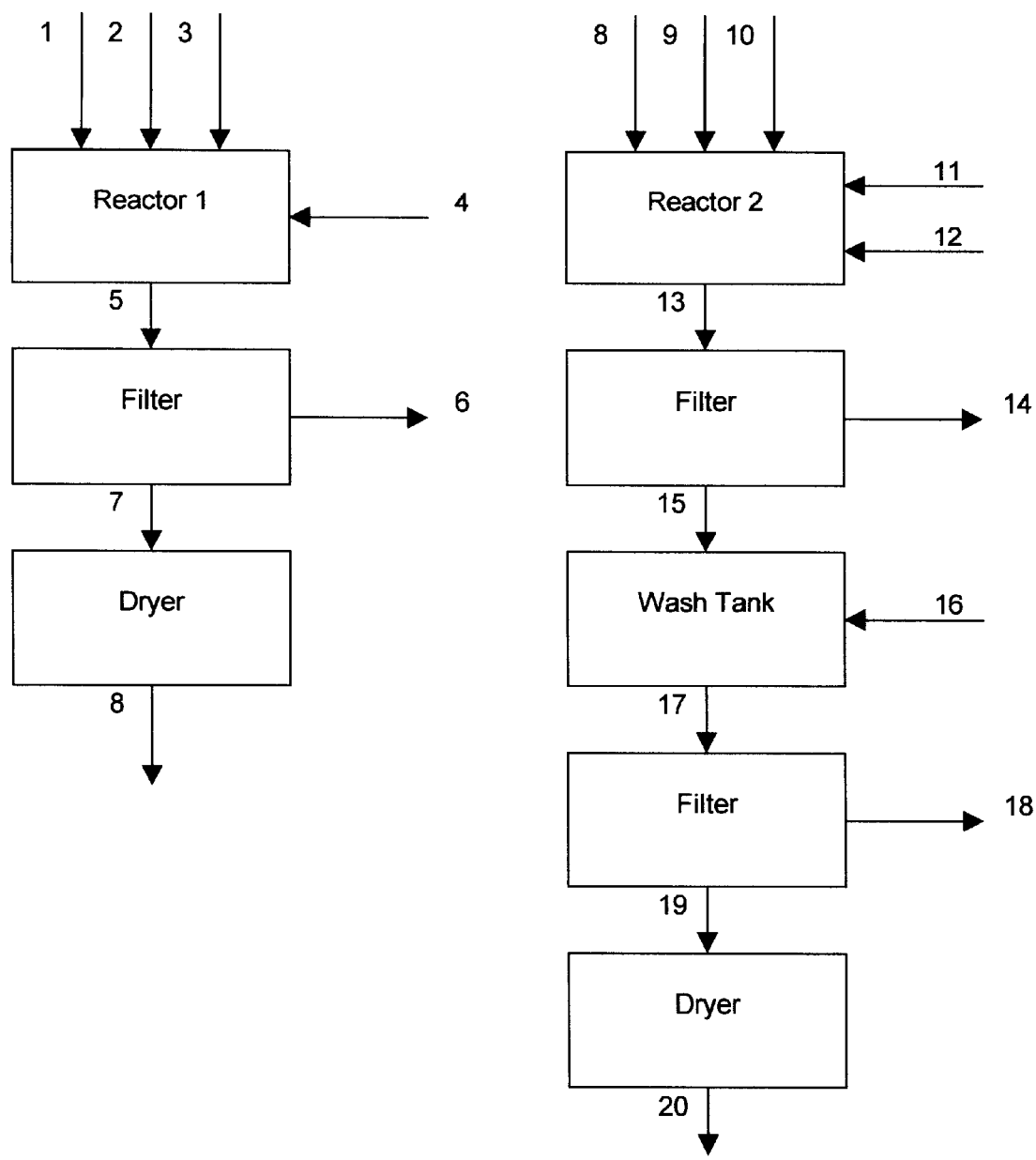
FIG. 1 is a process flow diagram showing the method of the present invention illustrating the steps leading to the production of betaine esters from betaine and fatty acid derived alcohol.

Turning now to the drawing, FIG. 1, there is shown in functional block diagram form a process for the improved synthesis of betaine esters from which there is little or no waste. This Product Flow Diagram is illustrative of a preferred embodiment. All streams are indicated by arrows with the overall steps being illustrated by the larger boxes to which the product streams are directed.

To produce the betaine ester one must first make the betaine hydrochloride. One mole of betaine 1 is reacted (reactor 1) with 1 mole of hydrochloric acid (HCl) 2 to form one mole of betaine hydrochloride. Betaine hydrochloride is dissolved in water 3 and concentrated HCl 2 is added to adjust the pH of the solution to 2. Ethanol 4 is added to help facilitate the growth of the betaine hydrochloride crystals. The solution 5 is kept chilled for up to 24 hours. The crystals 7 are filtered (filter 1) and the water-ethanol juice 6 is recycled to the next batch. The crystals 8 are dried in a vacuum dryer (dryer 1).

One mole of the betaine hydrochloride 8 is reacted with one mole of aliphatic alcohol 9 to yield one mole of betaine ester. The aliphatic alcohol is used in excess to drive the reaction to completion. The alcohol is placed in the reactor (reactor 2) and heat is applied to melt the alcohol. The betaine hydrochloride 8 and acid catalyst 10 is added. Agitation is applied and the temperature is set to 120° C. Once the reaction mixture reaches temperature it takes up to 24 hours for the esterification reaction to be complete. After the reaction is complete the reaction is cooled to 60° C. and neutralizing agent, such as potassium carbonate 11 is added to neutralize the acid catalyst.

The product is purified by first washing with hot water 12. The mixture is cooled to room temperature and two layers form. The product layer, which is the top layer, contains the product and unreacted aliphatic alcohol and the aqueous layer contains potassium sulfate and unreacted betaine hydrochloride. The mixture 13 is filtered (filter 2) and the aqueous layer 14 is saved for later processing. The product layer 15 is dissolved in hot ethyl acetate 16 to remove any unreacted aliphatic alcohol. The solution 17 is cooled and filtered (filter 3). The ethyl acetate layer 18 is saved for later processing to recover the aliphatic alcohol and ethyl acetate in order to to recover the hexadecanol and ethyl acetate in order to recycle both materials. The betaine ester 19 is dried (dryer 3) and the betaine ester product 20 analyzed.

To produce the specific betaine ester (ethanaminium, 2-(hexadecyloxy)N,N,N-trimethyl-2-oxo, chloride) one must first make the betaine hydrochloride. One mole of betaine is reacted with 1 mole of hydrochloric acid (HCl) to form one mole of betaine hydrochloride. Betaine hydrochloride is dissolved in water and concentrated HCl is added to adjust the pH of the solution to 2. Ethanol is added to help facilitate the growth of the betaine hydrochloride crystals. The solution is kept chilled for 24 hours. The crystals are filtered and the water-ethanol juice is recycled to the next batch. This can not be done indefinitely. One of the benefits of the process in this instant invention is that all materials are assimilated readily by natural microorganisms. The betaine hydrochloride and degradation products (dimethyl and monomethyl glycine) in the wash are readily biodegradable. Eventually some will have to go to waste and some fresh water added. The fraction that does go to waste would be distilled to recover ethanol and the aqueous phase discarded. The crystals are dried in a vacuum dryer.

One mole of the betaine hydrochloride is reacted with one mole of hexadecanol to yield one mole of betaine ester (ethanaminium, 2-(hexadecyloxy)-N,N,N-trimethyl-2-oxo, chloride). Hexadecanol is used in excess to drive the reaction to completion. The hexadecanol is placed in the reactor and heat is applied to melt the alcohol. The betaine hydrochloride and acid catalyst is added. Agitation is applied and the temperature is set to 120° C. Once the reaction mixture reaches temperature it takes 24 hours for the esterification reaction to be complete. After the reaction is complete the reaction is cooled to 60° C. and potassium carbonate is added to neutralize the acid catalyst.

The product is purified by first washing with hot water. The mixture is cooled to room temperature and two layers form. The product layer, which is the top, contains the product and unreacted hexadecanol and the aqueous layer contains potassium sulfate and unreacted betaine hydrochloride. The mixture is filtered and the aqueous layer is saved for later processing. The product layer is dissolved in hot ethyl acetate to remove any unreacted hexadecanol. The solution is cooled and filtered. The ethyl acetate layer is saved for later processing to recover the hexadecanol and ethyl acetate in order to recycle. The product is dried and analyzed. The product is characterized by melting point determination, density, solubility determinations and FT-IR analysis.

Except for minor processing losses, everything in the process is either product, recycled or recovered. An additional loss is a small portion of the solvent discarded in the betaine hydrochloride preparation. The potassium sulfate formed from neutralization of the acid catalyst is recovered from the aqueous fraction and can be sold as a by-product for fertilizer, either as potassium sulfate or calcium sulfate.

The aqueous solution from the neutralization step initially contains betaine hydrochloride and potassium sulfate. If the pH of this solution is raised above approximately 6.5, the hydroxide of trimethyl glycine can be recovered by removal of water since one gram of this material requires 160 milliliters of water to maintain solubility. The aqueous solution would contain the potassium sulfate which could be recovered. The potassium sulfate would contain <5% of the hydroxide of trimethyl glycine by weight. The hydroxide of trimethyl glycine is converted back to betaine hydrochloride for subsequent use by addition of HCl as in its initial preparation.

Alternatively one could remove sulfate from the solution by ion exchange or addition of calcium salts. This would leave potassium chloride (KCl) in solution whereupon the pH could be increased to remove the betaine as detailed above. Since KCl is more soluble than potassium sulfate the amount of betaine lost to the recovery of KCl would be <2% of the weight of the KCl.

The water is removed by vacuum distillation and the betaine HCl is recycled back to the esterification reaction. The ethyl acetate is distilled and the hexadecanol is also recycled back to the reaction. The ethyl acetate is used to wash the next batch of product. The reaction yields are between 20 and 40%, however the overall yield based on recycling exceeds 90%. The process is easy to operate in a batch-processing mode and can be scaled up to the desired level.

EXAMPLE 1

150.23 grams of hexadecanol were placed in a three neck one-liter flask. The heat was turned on to 50° C. to melt the hexadecanol. A mechanical stir bar is added. When the hexadecanol was all melted the stirrer was turned on. 50.01 grams of betaine hydrochloride are added slowly. Sulfuric acid was used as the catalyst and 5.00 grams was added. The temperature was increased to 120° C. The color of the reaction was light tan color when the reaction reached constant temperature. After 24 hours the heating mantle was removed and the reaction was cooled to 60° C. and 13.52 grams of potassium carbonate was added very slowly to neutralize the reaction. The reaction mixture was transferred to a one-liter beaker and 300 ml of hot distilled water was added. An additional 300-ml of hot distilled water was used to quantitatively transfer the product. Two layers formed, a solid-emulsion layer on top and an aqueous layer on the bottom. The product was vacuum filtered and washed four times with distilled water. The solid layer was transferred to a beaker and completely melted. Hot ethyl acetate was added (750 milliliters). The solution was mixed and allowed to cool to room temperature. Two layers formed, a solid layer and a liquid layer. The mixture was filtered and the solids were washed three times with ethyl acetate. The solids were placed in a dessicator to remove all of the ethyl acetate. The betaine ester was characterized by melting point, density, and FT-IR. The melting point was 57–62° C., the density was 0.35 g/ml and the FT-IR scan showed the ester peak at 1748 $cm^{-1}$ wavenumbers, alkyl amine peak was present at 1471 $cm^{-1}$ and alkane stretching was at 2851 $cm^{-1}$ wavenumbers. The direct reaction yield was 26.1%.

Unreacted hexadecanol was recovered by distilling the ethyl acetate. The ethyl acetate is used for washing the next batch of betaine ester. The water from the water wash was evaporated and the potassium sulfate recovered. Unreacted betaine hydrochloride was recovered.

EXAMPLE 2

A 151.44 grams of hexadecanol was melted and poured into a three-neck liter flask with a mechanical stirrer and hot plate. 50.41 grams of betaine hydrochloride were added slowly to the reactor and 5.01 grams of sulfuric acid was added. The temperature was set to 130° C. The color was a light tan. After 24 hours the reaction was cooled to 60° C. and 13.63 grams of potassium carbonate was added to neutralize. The product was transferred to a beaker and washed with four times the amount of hot distilled water. The product was filtered and the aqueous layer was saved for later recovery. The product was melted and 800 ml of hot ethyl acetate was added to remove the unreacted hexadecanol. The solution was cooled to room temperature and two layers formed. The solids were filtered and washed with ethyl acetate and placed in the dessicator to dry. The ethyl acetate-hexadecanol solution was saved for later recovery. The yield was 20.4%.

EXAMPLE 3

In this example some of the previously recovered hexadecanol and ethyl acetate was used. A 120.88 grams of recovered hexadecanol and 31.00 grams of fresh hexadecanol were melted and transferred to a reaction flask. Then 50.03 grams of betaine hydrochloride and 8.5 grams of sulfuric acid were added. The temperature was set to 120° C. After 24 hours the reaction mixture was cooled and neutralized with 23.10 grams of potassium carbonate. The mixture was transferred to a beaker and 500 ml of hot distilled water was added to wash. It was cooled to room temperature and the solids were filtered and washed with water. The resulting product was then melted and washed with 600 ml of hot ethyl acetate. This solution was cooled to room temperature and two layers formed. The product was filtered and dried and the reaction yield was 33.0%.

EXAMPLE 4

In this example the temperature of the reaction was 125° C. and the reaction size was doubled. Thus, 300.66 grams of hexadecanol was melted and transferred to a reaction flask. The betaine hydrochloride and the sulfuric acid, 100.30 grams and 11.01 grams respectively, were added to the flask. The mixture was agitated and heated for 24 hours at 125° C. At the end of 24 hours the reactor was cooled and the mixture was neutralized with 29.18 grams of potassium carbonate. The product was transferred to a beaker and washed with 1000 milliliters of hot distilled water. The mixture cooled and two layers formed. The solids were filtered and washed with water. The solids were melted and a liter of hot ethyl acetate was added to remove the excess hexadecanol. The solution was cooled and again two layers formed. The solids were filtered and washed with ethyl acetate and placed in the dessicator to dry. The reaction yield was 37.2%. The ethyl acetate was distilled and saved for a later batch and the excess hexadecanol was recovered.

EXAMPLE 5

In this reaction the temperature was set at 120° C. and the reaction size was increased by a factor of 5. Hexadecanol (750.0 grams) was melted and placed into a five-liter flask. Betaine hydrochloride (251.14 grams) were slowly added along with 29.12 grams of sulfuric acid. The temperature was set to 120° C. and the reaction proceeded for 24 hours. At the end of 24 hours the reaction was cooled and 74.63 grams of potassium carbonate was added to neutralize the acid. The product was purified in the same matter as above and the reaction yield increased to 40.2%.

Having described in detail a preferred embodiment of our invention, it will now be apparent to those having ordinary skill in the art that numerous modifications can be made therein without departing from the scope of the invention as defined in the following claims.

We claim:

1. A method of synthesis of betaine esters comprising:
   (a) adding hydrochloric acid to a glycine betaine in a sufficient quantity to produce one mole of betaine hydrochloride for each mole of hydrochloric acid;
   (b) dissolving said betaine hydrochloride in water and adding concentrated hydrochloride acid to adjust pH to 2;
   (c) chilling said solution for up to 24 hours, adding ethanol to facilitate formation of betaine hydrochloride crystals, filtering said betaine hydrochloride crystals, and drying said betaine hydrochloride crystals,
   (d) recycling the water-ethanol solution fraction for use in the next batch;
   (e) charging a reactor with a fatty acid derived alcohol and applying heat to liquidity the fatty acid derived alcohol,
   (f) adding said betaine hydrochloride crystals and an acid catalyst;
   (g) applying agitation and maintaining temperature;
   (h) reacting mixture until esterification is complete, cooling said mixture, and adding an neutralization agent to neutralize the acid catalyst;
   (i) purifying, crystallizing and drying the betaine ester product.

2. A method of synthesis as in claim 1 wherein the glycine betaine is a by-product of beet sugar refining.

3. A method of synthesis as in claim 1 wherein the fatty acid derived alcohol is selected from a group containing 12 to 18 carbons and said esterification catalyst is sulfuric acid.

4. The method of claim 3 wherein said fatty acid derived alcohol is hexadecanol.

5. A method of synthesis as in claim 1 wherein said temperature is between 120 degrees C. and 130 degrees C.

6. A method of synthesis as in claim 1 wherein said neutralization agent is potassium carbonate.

7. The method of synthesis as in claim 1 wherein ethyl acetate is used in purifying said betaine ester.

* * * * *